US011642833B2

(12) United States Patent
Vulgaris et al.

(10) Patent No.: US 11,642,833 B2
(45) Date of Patent: May 9, 2023

(54) CANNULA BUMP

(71) Applicant: Smiths Medical ASD, Inc., Plymouth, MN (US)

(72) Inventors: Michael C. Vulgaris, West Hartford, CT (US); James Muskatello, Southington, CT (US); Harsh D. Chheda, Cheshire, CT (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 671 days.

(21) Appl. No.: 16/580,875

(22) Filed: Sep. 24, 2019

(65) Prior Publication Data

US 2020/0094464 A1 Mar. 26, 2020

Related U.S. Application Data

(60) Provisional application No. 62/736,253, filed on Sep. 25, 2018.

(51) Int. Cl.
*B29C 57/04* (2006.01)
*A61M 25/06* (2006.01)
(Continued)

(52) U.S. Cl.
CPC ............ *B29C 57/04* (2013.01); *A61M 5/329* (2013.01); *A61M 25/0606* (2013.01);
(Continued)

(58) Field of Classification Search
None
See application file for complete search history.

(56) References Cited

U.S. PATENT DOCUMENTS 2,958,929 A * 11/1960 David ...................... H01R 4/20
29/862
3,540,112 A * 11/1970 Knox .................. A61M 5/3286
72/370.1
(Continued)

FOREIGN PATENT DOCUMENTS

KR 10-1313827 B1 10/2013

OTHER PUBLICATIONS

"Poisson's Ratio." Wikipedia, Wikimedia Foundation, Mar. 16, 2018, https://web.archive.org/web/20180316125905/https://en.wikipedia.org/wiki/Poisson's_ratio. (Year: 2018).*

(Continued)

*Primary Examiner* — Alison L Hindenlang
*Assistant Examiner* — Andrés E. Behrens, Jr.
(74) *Attorney, Agent, or Firm* — Louis Woo

(57) ABSTRACT

A method of creating a feature on a needle. The method comprising the steps of providing a needle having a sharpened distal end for insertion into an insertion site on a subject, a proximal end, and a tubular wall defining an inner diameter and an outer diameter; gripping a distal portion of the needle about the outer diameter; gripping a proximal portion of the needle about an outer diameter; and applying a compressive force between the distal portion and the proximal portion sufficient to effect an outward buckling of the tubular wall, thereby increasing an outer diameter of the tubular wall between the distal portion and the proximal portion.

12 Claims, 2 Drawing Sheets

(51) Int. Cl.
*A61M 5/32* (2006.01)
*A61M 25/08* (2006.01)
*B29L 31/60* (2006.01)
*B29L 31/00* (2006.01)

(52) U.S. Cl.
CPC .... *A61M 25/0693* (2013.01); *B29L 2031/606* (2013.01); *B29L 2031/7544* (2013.01)

(56) References Cited

U.S. PATENT DOCUMENTS

| | | | | |
|---|---|---|---|---|
| 5,099,676 | A * | 3/1992 | Proto | B21J 13/02 72/416 |
| 5,722,991 | A * | 3/1998 | Colligan | B21G 1/08 29/748 |
| 6,914,212 | B2 | 7/2005 | Adams | |
| 7,002,098 | B2 | 2/2006 | Adams | |
| 8,439,877 | B2 * | 5/2013 | Burkholz | A61M 5/329 604/110 |
| 8,474,300 | B2 | 7/2013 | McKinnon et al. | |
| 8,936,575 | B2 * | 1/2015 | Moulton | A61M 25/0612 604/164.08 |
| 2005/0080378 | A1 * | 4/2005 | Cindrich | A61M 25/0625 604/164.01 |
| 2010/0305519 | A1 * | 12/2010 | McKinnon | A61M 25/0612 604/523 |
| 2011/0011149 | A1 * | 1/2011 | McKinnon | A61M 5/329 72/367.1 |
| 2014/0228778 | A1 * | 8/2014 | Ma | A61M 39/221 29/428 |
| 2014/0276462 | A1 * | 9/2014 | Vincent | A61M 39/26 29/428 |
| 2015/0190570 | A1 * | 7/2015 | Teoh | A61M 39/0613 29/428 |

OTHER PUBLICATIONS

International Preliminary Report on Patentabiltiy for PCT/US2019/052627.
Search Report dated Jan. 10, 2020 for Application No. PCT/US2019/052627, 11 pages.
Email from Thomas Kuracina of InjectiMed dated Jan. 11, 2021 with attached memo.
Kuracina memo attached to Kuracina email of Jan. 11, 2021.
Printout from Website of injectiMed's Front Line Medical Products Company entitled "Features & Benefits of the SafetyNET Guidewire Introducer".

* cited by examiner

CANNULA BUMP

RELATED APPLICATION

The present application claims the benefit of U.S. Provisional Application No. 62/736,253 filed Sep. 25, 2018, which is hereby incorporated herein in its entirety by reference.

TECHNICAL FIELD

The present disclosure relates generally to infusion devices, such as intravenous needles, used in combination with over the needle peripheral intravenous catheters, and more particularly to methods configured to provide a feature on an outer surface of the needle while generally preserving the cross sectional profile of the inner surface of the needle.

BACKGROUND

Intravenous (IV) therapy is a versatile technique used for the administration of medical fluids to and withdrawal of bodily fluids from patients. IV therapy has been used for various purposes, such as the maintenance of blood and electrolyte balance, the transfusion of blood, the administration of nutritional supplements, chemotherapy, and the administration of drugs and medications. These fluids, collectively referred to herein as medicaments, may be administered intravenously by injection through a hypodermic needle, or intermittently or continuously by infusion using a needle or catheter. A common intravenous access device utilized by clinicians is the Peripheral Intravenous Catheter (PIVC).

A PIVC is made of a soft, flexible plastic or silicone, generally between fourteen to twenty-four gauge in size. In the conventional venipuncture procedure, a catheter is inserted into a vein in the patient's hand, foot, or the inner aspect of the arm or any vein in the body that will accept an IV catheter. Typically PIVCs are "over the needle" catheters, where a catheter is coaxially placed over a needle of an intravenous catheter insertion device. In order to properly place the catheter into the patient's vein, the needle is used to puncture the skin, tissue, and vein wall to provide a path for placement of the catheter into the vein.

Placement of the catheter generally includes preparation of a biological site of the patient. Often a tourniquet is applied proximal to the biological site and a variety of techniques can be used to dilate the patient's vein. While wearing disposable gloves, the clinician cleanses the biological site and a vein is retracted or anchored by placing a thumb over the vein about fifty to seventy five mm distal to the site. The needle and catheter are introduced into the vein by inserting a beveled sharpened tip of the needle into the vein at about a twenty to thirty degree angle, with the bevel facing up in order to pierce one wall of the vein. The catheter thus rides with the needle through the skin, tissue, and vein wall into the patient's vein. To finish placement, the needle and catheter are lowered towards the skin to decrease the entry angle, and the catheter is advanced slightly into the vein. Once the catheter is satisfactorily positioned within the vein, the needle is typically withdrawn from inside the catheter, and the connection between the catheter and the intravenous catheter device is loosened, so that the catheter can be advanced further into the vein as desired. The catheter can then be secured in place on the biological site by adhesive tape, while the intravenous catheter insertion device is properly disposed of in a sharps container.

In some cases, the needle can include a feature having a larger cross sectional size and/or shape than portions of the needle that lie in proximity to the feature. The needle feature (alternatively referred to as needle or cannula bump) can serve as an aid in triggering certain safety features designed to reduce the occurrence of unintended needle sticks. Needle features can be created by crimping opposed sides of the needle, or otherwise disrupting the structure of the needle, so that a portion of the outer surface of the needle extends to a larger radial position than other portions of the outer surface of the needle, as measured from the center of the needle axis. An example of such a method of creating a needle feature is disclosed in U.S. Pat. No. 8,474,300, the disclosure of which is hereby incorporated by herein by reference in its entirety. Alternatively, the feature can be created by adding material, such as a band of metal, to the exterior of the needle. An example of such a method of creating a needle feature is disclosed by U.S. Pat. No. 6,914,212, the disclosure of which is hereby incorporated by herein by reference in its entirety.

SUMMARY OF THE DISCLOSURE

While methods exist for providing a feature on a needle, challenges still exist. In particular, needle crimping methods, such as that disclosed in U.S. Pat. No. 8,474,300, can reduce the lumen of the needle, such that the flow of bodily fluid therethrough is inhibited. Where the needle insertion device includes a flashback indicator configured to confirm entry of the needle into a vein of a patient, inhibiting flow within the lumen is not desirable. Alternative methods of adding material to the exterior of the needle can be time-consuming, and can significantly add to the cost of producing a catheter insertion device. The present disclosure addresses these concerns.

Embodiments of the present disclosure provide a method of creating a feature on a needle that does not decrease the inner diameter or lumen of the needle. Moreover, embodiments of the present disclosure provide a method of creating a feature on a needle that can be completed quickly, thereby improving efficiency in manufacturing, and aiding in the reduction of cost. In particular, embodiments of the present disclosure provide a method of applying a compressive force along a longitudinal axis of the needle to cause a buckling and/or outward expansion of the needle wall.

One embodiment of the present disclosure provides a method of creating a feature on a needle, including the steps of: providing a needle having a sharpened distal end for insertion into an insertion site on a subject, a proximal end, and a tubular wall defining an inner diameter and an outer diameter; gripping a distal portion of the needle about the outer diameter; gripping a proximal portion of the needle about the outer diameter; and applying a compressive force between the distal portion and the proximal portion sufficient to affect an outward buckling of the tubular wall, thereby increasing an outer diameter of the tubular wall between the distal portion and proximal portion along at least a portion of the outer diameter.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1:
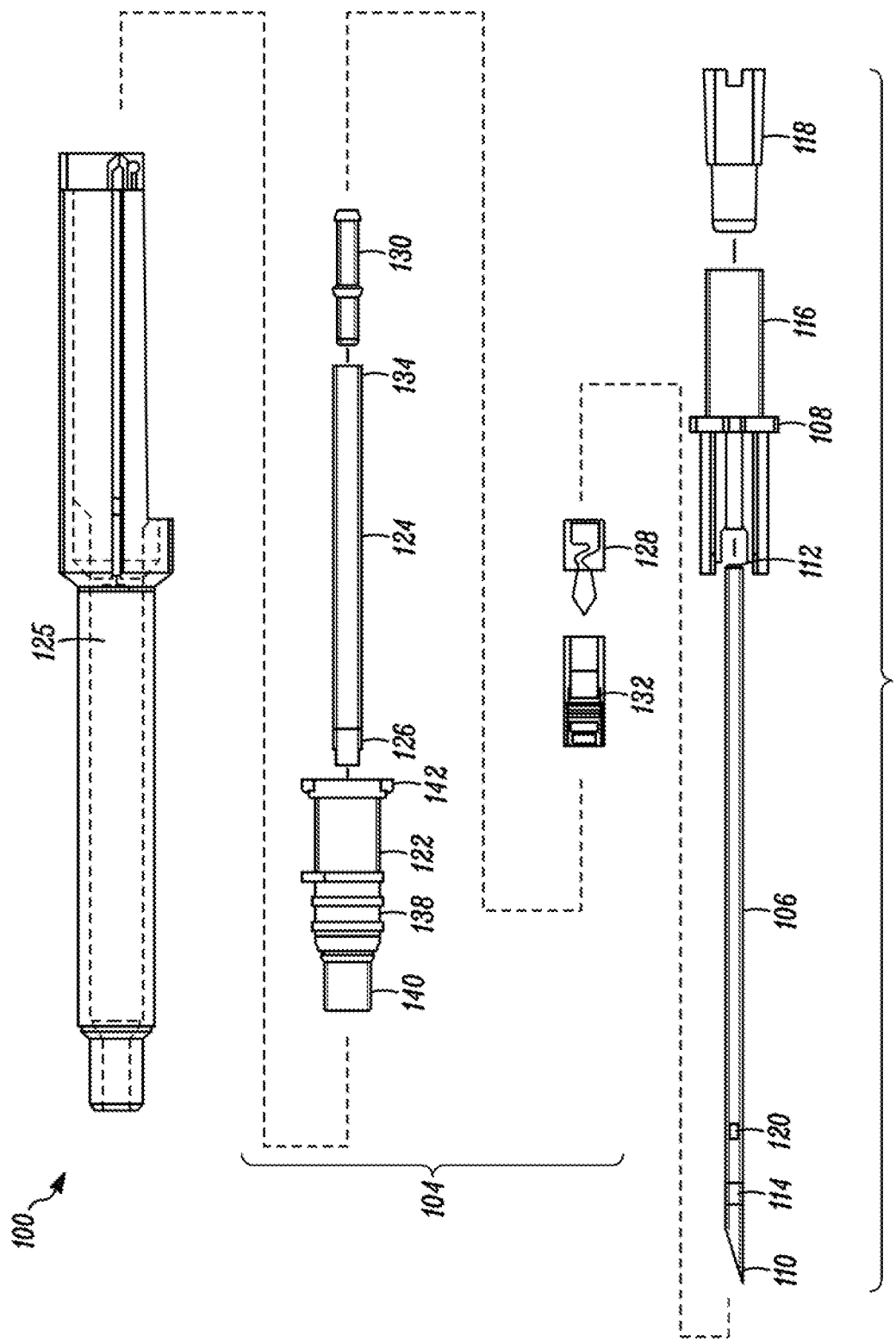
FIG. 1 is an exploded view depicting a safety catheter insertion assembly, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, an exploded view depicting a safety catheter insertion assembly 100 is depicted in accordance with an embodiment of the disclosure. The safety catheter assembly 100 can include a catheter insertion device 102 and a catheter assembly 104. The catheter insertion device 102 can include an insertion or needle cannula 106 operably coupled to a needle hub 108. The needle cannula 106 can include an elongate cylindrically shaped metal structure defining a tubular wall 107 that extends between the sharpened distal needle tip 110 and a proximal end 112. The tubular wall 107 can define an inner diameter 109 and an outer diameter 111. The sharp distal needle tip 110 can be constructed and arranged to pierce the skin of a subject during catheter insertion. For example, in one embodiment, the sharp distal tip 110 can include a V-point designed to reduce the penetration force used to penetrate the needle 106 and a portion of the catheter insertion assembly 104 through the skin, tissue, and vein wall of a subject. In one embodiment, the length of the needle 106 can be extended to aid in the insertion of the catheter assembly 104 into obese patients.

The proximal end 112 of the needle cannula 106 can be operably coupled to the needle hub 108. The needle hub 108 can include a gripping portion for manipulation by a clinician. In one embodiment, the catheter insertion device 102 can be constructed to provide a visual indication of flashback when the sharpened distal tip 110 of the needle 106 enters the vein of a subject. In this embodiment, the needle hub 108 includes a flash chamber 116 in fluid communication with the lumen of the needle. When the sharp distal tip 110 enters a vein during catheter insertion, blood or bodily fluid enters the needle lumen from the vein and flows proximally through the needle 106 into the flash chamber 116. The flash chamber 116 can be sealed at one end by a flash plug 118. The flash plug 118 can be made out of an air permeable, hydrophilic material that enables the passage of air, but inhibits the passage of liquid. Air that resides in the needle lumen and flash chamber 116 is therefore pushed through the flash plug 118 by the incoming blood, until the blood reaches the flash plug 118 or is otherwise stopped. The needle hub 108, or portions thereof, can be constructed of a clear or translucent material configured to enable a clinician to view the presence of blood within the flash chamber 116. In this respect, the clinician can be alerted when the needle has entered the vein of the subject by the presence of blood in the flash chamber 116.

In one embodiment, features of the catheter insertion device 102, other than a flash chamber 116, can provide an indication that the sharp distal tip 110 has entered the vein of a subject. For example, the needle cannula 106 can include a notch 120. In this embodiment, blood flow enters the needle lumen where the sharp distal tip 110 enters the vein. As blood flows proximally in the needle lumen, some blood passes through the notch 120 and into an annular space that lies between an exterior of the needle 106 and an interior of the catheter assembly 104. The presence of blood in the annular space can be viewed by a clinician through a clear or translucent portion of the catheter assembly 104, thereby providing an indication the sharpened distal tip 110 is present in a vein.

Figure 2A:
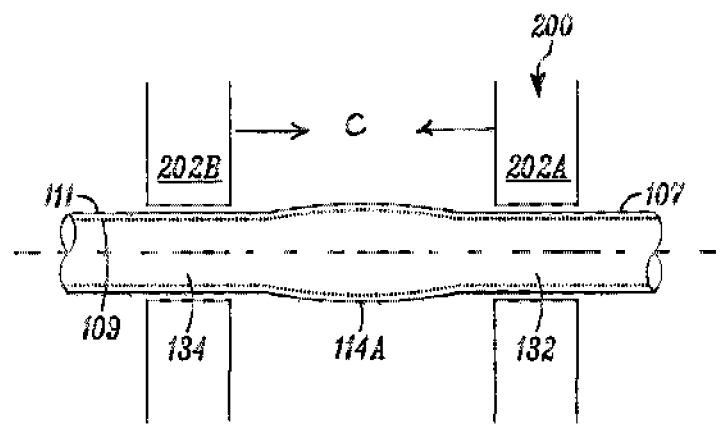
FIG. 2A is a cross-sectional view depicting a needle including a symmetrical needle feature, in accordance with an embodiment of the disclosure.
Figure 2B:
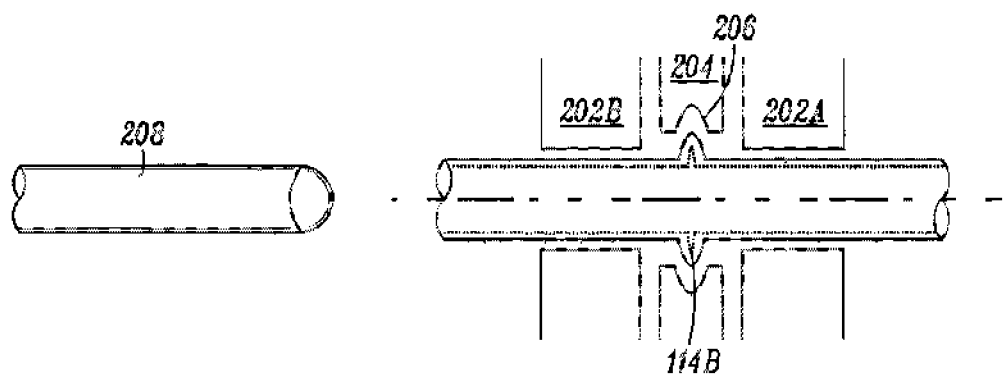
FIG. 2B is a cross-sectional view depicting a needle including a disk shaped needle feature, in accordance with an embodiment of the disclosure.
Figure 2C:
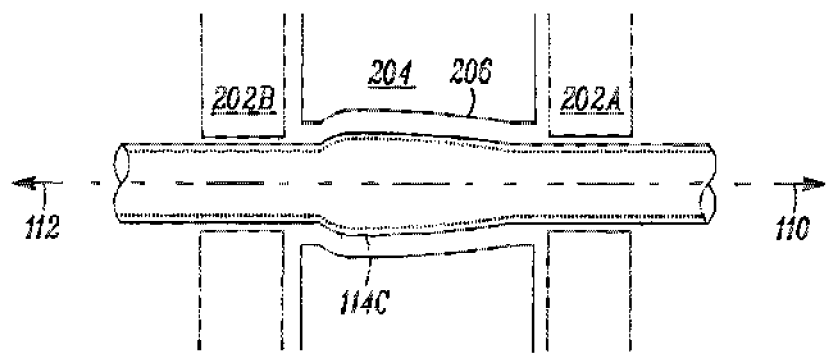
FIG. 2C is a cross-sectional view depicting a needle including an asymmetrical needle feature, in accordance with an embodiment of the disclosure.

The needle cannula 106 can further include a feature 114 having a different cross-sectional size and/or shape than other portions of the needle cannula 106 positioned proximal to the feature 114. Referring to FIG. 2A-C, cross-sectional views depicting a needle cannula 106 including a feature 114 are depicted in accordance with embodiments of the disclosure. The needle feature 114 (alternatively referred to as a needle bump or cannula bump) can be created by applying a compressive force along a longitudinal axis of the needle cannula 106, so that the outer diameter 111 of the tubular wall 107 buckles, thereby extending outwardly to a larger radial position than other portions of the needle cannula 106 in proximity to the feature 114, as measured from the longitudinal axis of the needle cannula 106.

For example, in one embodiment, the needle cannula 106 can be gripped by a crimping device 200 configured to apply a compressive force C to the needle cannula to affect an outward buckling of the tubular wall 107. In one embodiment, the crimping device 200 can include a first gripping member 202A configured to grip a distal portion 132 of the needle cannula 106, and a second gripping member 202B configured to grip a proximal portion 134 of the needle cannula 106 to effect the compressive force C by moving the gripping members 202A and 202B toward each other as per shown by the converging directional arrows shown in FIG. 2A. In some embodiments, gripping members 202A and 202B can form portions of a single apparatus configured to apply a compressive force C between gripping members 202A and 202B. In other embodiments, at least one of the distal portion 132 and/or proximal portion 134 can be positioned in a stabilizing vice (not depicted) against which the crimping device 200 can apply a compressive force C.

In some embodiments, an optional form 204 (as depicted in FIGS. 2B and 2C) can be positioned in proximity to the outer diameter 111 of the needle cannula 106 between the distal portion 132 and the proximal portion 134. The optional form 204 can be configured to inhibit expansion of the outer diameter 111 beyond a desired shape and/or size. In one embodiment, the form 204 can have a contoured surface 206 configured to at least partially surround the outer diameter 111 of the needle cannula 106, thereby enabling buckling onto the needle cannula 106 under a compressive force while restricting expansion of the outer diameter 111 to the contours of the contoured surface 206. Accordingly, the contoured surface 206 of the form 204 can dictate the overall shape and/or size of the needle feature 114. For example, in one embodiment, the form 204 can be utilized to create a symmetrical cannula bump 114A (such as that depicted in FIG. 2A). In one embodiment, an optional stylus 208 can be inserted into the inner diameter 109 of the needle cannula 106 to inhibit narrowing of the inner diameter 109 and/or inhibit the needle cannula 106 from collapsing during axial compression.

In some embodiments, the contoured surface 206 can define a shallow symmetrical curve. In other embodiments, the contoured surface 206 can be configured define a steep symmetrical curve, which in some embodiments can enable the tubular wall 107 to fold over upon itself, thereby effectively creating a disk or ring 114B (as depicted in FIG. 2B) at least partially surrounding the needle cannula 106.

In one embodiment, the contoured surface 206 can be configured to enable the outer diameter 111 of the tubular wall 107 to expand or buckle radially outward by at least 0.0001 of an inch. In another embodiment, the contoured surface 206 can be configured to enable the outer diameter 111 of the tubular wall 106 to expand or buckle radially outward by between about 0.0002 of an inch and about 0.0004 of an inch; although other radial expansion dimensions are also contemplated.

In one embodiment, the contoured surface 206 can be configured to create an asymmetrical cannula bump 114C (such as that depicted in FIG. 2C), such that a portion of the cannula bump 114C in proximity to the proximal end 112 of the needle cannula 106 increases in diameter at a faster rate than a portion of the cannula bump 114 in proximity to the distal needle tip 110 of the needle cannula 106. In some embodiments, the asymmetrical cannula bump 114C can be configured to enhance the effect of the cannula bump 114C on a corresponding actuating mechanism, such as a needle tip capture actuating mechanism or other actuatable feature. In some embodiments, the asymmetrical cannula bump 114 can be configured to enable the actuating mechanism to slide proximally over the cannula bump 114C towards the proximal end 112 of the needle cannula 106, while inhibiting the actuating mechanism from sliding distally over the cannula bump 114B towards the distal needle tip 110 of the needle cannula 106, thereby inhibiting the actuating mechanism from sliding distally off the distal needle tip 110 of the needle cannula 106.

In one embodiment, the feature 114 can extend radially outward around an entire perimeter for circumference of the outer diameter 111. In some embodiments, the radial extension can be substantially uniform in height. In such embodiments, the radial outward extension of feature 114 around the entire needle cannula 106 can serve to further inhibit the actuating mechanism from sliding distally over the cannula bump 114, particularly in comparison to cannula bumps which only extend along one or more sides and/or quadrants of the outer diameter 111. These noted advantages of the cannula bump 114 can apply to various types of actuating mechanisms, such as needle tip capture actuating mechanisms, needle retraction actuation mechanisms, catheter hub release mechanisms, sealing valve actuators, and the like.

In various tests performed by the Applicant, cannula bumps created via the methods disclosed herein were found to display a high degree of uniformity, particularly in comparison to the creation of cannula pumps via other methods. Accordingly, creation of cannula bumps via the methods disclosed herein can be utilized to improve quality control, and reduce manufacturing burdens, such as visual inspections, during production.

Methods of creating a cannula bump as disclosed herein can be utilized to form cannula bumps or features on needles and catheter insertion devices produced by companies such as Arizant, Argon Medical Corp., B. Braun Melsungen A G, Becton Dickinson and Company, C. R. Bard, Inc., Carefusion 303, Inc., Easter Medikit, Medical Components, Inc., OptiScan Biomedical Corp., Poly Medicure, Retractable Technologies, Tangent Medical Technologies LLC, Teleflex Medical, Inc., Terumo Kabushiki Kaisha, Vascular Pathways, Inc., Vigmed A B, and Vygon, among others.

With continued reference to FIG. 1, an exemplary embodiment of a catheter assembly 104 can include a catheter hub 122, a catheter tube 124, a needle tip capture mechanism 128, and actuator 130, and a seal member 132. In some embodiments, the catheter assembly 104 can further include a wing assembly, an extension tube, an extension tube clamp, a needleless connector, and/or a vent cap (not depicted). Accordingly, the catheter assembly 104 can include a blood control feature configured to inhibit blood from escaping after withdrawal of the needle cannula 106, thereby reducing the risk of exposure of blood or other bodily fluids to clinicians, particularly a consideration of sensitivity where blood-borne diseases may be present. Additional embodiments of the catheter assembly 104 can inhibit the introduction of unwanted contaminants into the interior of the catheter assembly 104 prior to the connection to an IV fluid supply.

The catheter tube 124 can extend from a tapered distal tube end 126 to a proximal hub end 134, where the catheter tube 124 can be operably coupled to the catheter hub 122. The catheter tube 124 can define a lumen configured to provide a fluid pathway between a vein of the subject and the catheter hub 122. In one embodiment, the catheter tube 124 can include a barium radio opaque line to ease in the identification of the catheter tube during radiology procedures.

The catheter hub 122 can include a catheter hub body 138 having a distal hub end 140 and a proximal end 142 and an internal wall defining an interior cavity therebetween. In one embodiment, the distal hub end 140 of the catheter hub body 138 is operably coupled to the proximal end 134 of the catheter tube 124, such that the lumen of the catheter tube is in fluid communication with the internal cavity of the catheter hub 122. In one embodiment, a proximal portion of the interior cavity can be shaped according to luer taper standards.

The actuator 130 can be secured proximal to the distal hub end 140 of the catheter hub 122, so as to extend axially within the interior cavity. In one embodiment, the proximal end 134 of the catheter tube can be secured within the interior cavity of the catheter hub 122 with the aid of the actuator 130. The seal member 132, alternatively referred to as a blood control valve 132, can also be secured within the interior cavity of the catheter hub, with the aid of actuator 130, such that the seal member 132 is axially shiftable relative to the actuator 130 between a closed-door sealed position, and an open or actuated position. Thus, the actuator 130 functions to both secure the catheter tube 124 to the catheter hub 122, and to support the seal member 132. In one embodiment, at least one of the needle tip capture mechanism 128 and/or actuator 130 can be positioned on the needle cannula 106 prior to formation of the feature 114, such that the feature 114 is formed distally to the needle tip capture mechanism 128 and/or actuator 130. In other embodiments, at least one of the needle tip capture mechanism 128 and/or actuator 130 can be proximally slid onto the needle cannula 106 over the feature 114 after formation. In these embodiments, an asymmetrical cannula bump (such as that depicted in FIG. 2C) can aid in enabling the needle tip capture mechanism 128 and/or actuator 130 in sliding proximally over the feature 114, while inhibiting distal movement of the needle tip capture mechanism 128 and/or actuator 130 back over the feature 114 in the opposite direction.

Various example embodiments of catheters are described herein for use in accessing the vein of a subject. It is to be appreciated, however, that the example embodiments described herein can alternatively be used to access the vascular of a subject at locations other than a vein, including but not limited to the artery of a subject. It is additionally to be appreciated that the term "clinician" refers to any individual that can perform a catheter insertion procedure with any of the example embodiments described herein or alternative combinations thereof. Similarly, the term "subject," as used herein, is to be understood to refer to an individual or object in which the catheter is to be inserted, whether human, animal, or inanimate. Various descriptions are made herein, for the sake of convenience, with respect to the procedures being performed by a clinician to access the vein of a subject, while the disclosure is not limited in this respect.

It is also to be appreciated that the term "distal," as used herein, refers to the direction along an axis that lies parallel to a needle cannula of a safety catheter assembly that is closest to the subject during catheter insertion. Conversely, the term "proximal," as used herein, refers to the direction lying along the axis parallel to the needle cannula that is further away from the subject when the catheter is inserted into the vein of the subject, opposite to the distal direction.

It should be understood that the individual steps used in the methods of the present disclosure may be performed in any order and/or simultaneously, as long as the method remains operable. Furthermore, it should be understood that the apparatus and methods of the present teachings can include any number, or all, of the described embodiments, as long as the apparatus methods remain operable.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A method of creating a feature on a needle, the method comprising:
providing a needle having a distal end for insertion into an insertion site on a subject, a proximal end, and a tubular wall defining an inner diameter and an outer diameter, the needle extending along a longitudinal axis;
gripping a distal portion of the needle about the outer diameter;
gripping a proximal portion of the needle about the outer diameter; and
applying a compressive force along the longitudinal axis between the distal portion and the proximal portion sufficient to effect an outward buckling of the tubular wall, thereby increasing an outer diameter of the tubular wall between the distal portion and the proximal portion.

2. The method of claim 1, wherein the compressive force causes at least a portion of the outer diameter of the tubular wall to buckle radially outwardly by at least 0.0001 of an inch.

3. The method of claim 2, wherein the compressive force causes a cross section of the outer diameter of tubular wall to form an asymmetrical curve.

4. The method of claim 3, wherein a portion of the asymmetrical curve in proximity to the proximal end of the needle increases a diameter at a faster rate than a portion of the asymmetrical curve in proximity to the distal end of the needle.

5. The method of claim 1, further comprising positioning a form configured to inhibit expansion of the outer diameter of the tubular wall beyond a desired shape in proximity to the outer diameter of the needle between the distal portion and the proximal portion.

6. The method of claim 1, further comprising positioning an actuating mechanism proximal to the proximal portion prior to applying the compressive force.

7. The method of claim 1, further comprising proximally sliding at least one of a needle tip capture mechanism or an actuator onto the needle cannula and over the feature after creation of the feature.

8. The method of claim 1, further comprising inserting a stylus into the inner diameter of the needle.

9. A method of making a needle, comprising the steps of:
positioning a cannula having a distal tip, a proximal end and a longitudinal body having a wall having an outer diameter along a longitudinal axis;
using at least one gripping member to grip a distal portion and a proximal portion of the needle;
applying a compressive force along the longitudinal axis between the distal portion and the proximal portion to cause the outer diameter of the wall between the distal portion and the proximal portion to extend radially from the longitudinal axis to form a needle feature that has a radial dimension different from the rest of the cannula.

10. The method of claim 9, wherein the using step further comprises the steps of:
gripping the distal portion by one gripping member;
gripping the proximal portion by another gripping member; and
moving the one and another gripping members toward each other to apply the compressive force along the longitudinal axis to form the needle feature.

11. The method of claim 9, wherein the using step further comprises the steps of:
gripping the distal portion by one gripping member;
gripping the proximal portion by another gripping member; and
moving one of the one and another gripping members toward the other of the one and another gripping members to apply the compressive force along the longitudinal axis to form the needle feature.

12. The method of claim 9, further comprising the step of:
positioning a form about the outer diameter of the cannula between the distal and proximal portions to configure the needle feature to a desired shape when the compressive force is applied axially between the distal and proximal portions.

\* \* \* \* \*